US008034982B2

(12) United States Patent
Martinez

(10) Patent No.: US 8,034,982 B2
(45) Date of Patent: Oct. 11, 2011

(54) ISOTOPICALLY TAGGED SYNONS FROM 2 CARBON PRECURSORS

(75) Inventor: Rodolfo A. Martinez, Santa Fe, NM (US)

(73) Assignee: New Mexico Highlands University, Las Vegas, NM (US)

( * ) Notice: Subject to any disclaimer, the term of this patent is extended or adjusted under 35 U.S.C. 154(b) by 632 days.

(21) Appl. No.: 12/035,871

(22) Filed: Feb. 22, 2008

(65) Prior Publication Data

US 2008/0269527 A1   Oct. 30, 2008

Related U.S. Application Data

(60) Provisional application No. 60/923,107, filed on Apr. 11, 2007, provisional application No. 60/948,359, filed on Jul. 6, 2007.

(51) Int. Cl.
   *C07C 43/00*   (2006.01)
(52) U.S. Cl. ............ 568/687; 568/28; 568/38; 568/58; 568/59; 568/581
(58) Field of Classification Search ................. None
   See application file for complete search history.

(56) References Cited

U.S. PATENT DOCUMENTS

2003/0158445 A1   8/2003   Martinez et al. ............. 568/28

FOREIGN PATENT DOCUMENTS

JP   2001039924   *   2/2001

OTHER PUBLICATIONS

Grue-Soerensen et al., {Biosynthetic Route to the Ephedra Alkaloids, Journal of the American Chemical Society (1994), 116(14), 6195-200}.*
Bartuska et al., {Carbon-13-carbon-13 coupling constants. IV. Isopropenyl system, Journal of Magnetic Resonance (1969-1992) (1972), 7(1), 36-47}.*
Dijkstra et al., {Rearrangements and fragmentations of phenyl styryl sulfides, Organic Mass Spectrometry (1982), 17(9), 430-8}.*
Proctor, David J., The Synthesis of Thiols, Selenas, Sulfides, Selenides, Sulfoxides, Selenoxides, Sulfones and Selenones; In J. Chem. Soc., Perkin Trans. 1999; 1:641-667.
PCT—Notification of Transmittal of the International Search Report and the Written Opinion of the International Searching Authority, or the Declaration, Date of Mailing Jul. 25, 2008.

* cited by examiner

*Primary Examiner* — Sudhakar Katakam
(74) *Attorney, Agent, or Firm* — Luis M. Ortiz; Kermit D. Lopez; Ortiz & Lopez, PLLC

(57) ABSTRACT

The use of vinyl sulfides, sulfoxides and sulfones in synthetic chemistry for the production of a wide variety of materials is well known. For example, phenyl vinyl sulfides, sulfoxides and sulfones have been used for the synthesis of important heterocycles, in combinatorial chemistry and as Diels-Alder adducts. Although these compounds have been used extensively for a variety of applications, the isotopically labeled versions have not been reported. A simple route for the isotopically labeled production of these important building blocks has been developed.

7 Claims, 5 Drawing Sheets

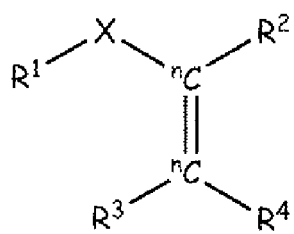

Where X = S, SO, SO$_2$ or O
R$^1$ = Alkyl or Aryl
R$^2$ = H, $^2$H, $^3$H, Alkyl or Aryl
R$^3$ = H, $^2$H, $^3$H, Alkyl or Aryl
R$^4$ = H, $^2$H, $^3$H, Alkyl or Aryl
n = 12, 13, 14

Fig. 7

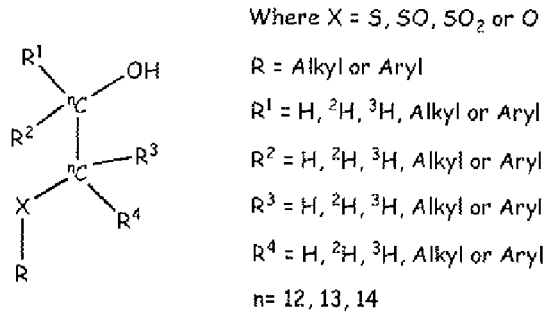

Where X = S, SO, SO$_2$ or O
R = Alkyl or Aryl
R$^1$ = H, $^2$H, $^3$H, Alkyl or Aryl
R$^2$ = H, $^2$H, $^3$H, Alkyl or Aryl
R$^3$ = H, $^2$H, $^3$H, Alkyl or Aryl
R$^4$ = H, $^2$H, $^3$H, Alkyl or Aryl
n = 12, 13, 14

Fig. 8

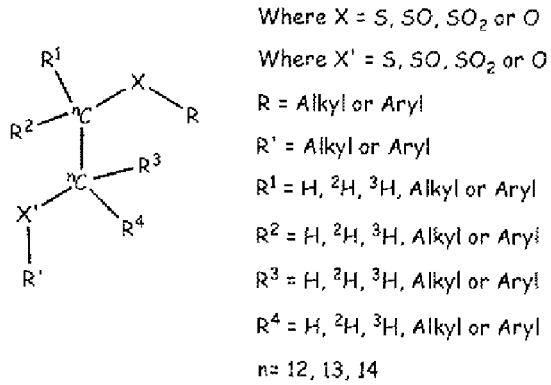

Where X = S, SO, SO$_2$ or O
Where X' = S, SO, SO$_2$ or O
R = Alkyl or Aryl
R' = Alkyl or Aryl
R$^1$ = H, $^2$H, $^3$H, Alkyl or Aryl
R$^2$ = H, $^2$H, $^3$H, Alkyl or Aryl
R$^3$ = H, $^2$H, $^3$H, Alkyl or Aryl
R$^4$ = H, $^2$H, $^3$H, Alkyl or Aryl
n = 12, 13, 14

Fig. 9

ISOTOPICALLY TAGGED SYNONS FROM 2 CARBON PRECURSORS

This patent application claims the priority and benefit of two U.S. Provisional Patent Applications the first being No. 60/923,107 filed Apr. 11, 2007 entitled "Carbon Labeled, Isotopically Labeled C13 Molecules and also deuterium Labeled Molecules Based on the Chemistry of C13 Methyl Phenyl Sulfide" and the second being No. 60/948,359 filed Jul. 6, 2007 and titled "Synthesis of Isotopically Tagged Synons". Both 60/923,107 and 60/948,359 are herein incorporated by reference.

TECHNICAL FIELD

The present invention relates to labeled compounds and more particularly to isotopically enriched alkyl and aryl vinyl sulfides, sulfoxides and sulfones, labeled with isotopes of carbon and helium. The isotopic tags can be carbon-13 or carbon-13 and hydrogen-2. The specific labeled compounds are produced from two carbon precursors.

BACKGROUND OF THE INVENTION

Vinyl sulfides, sulfoxides and sulfones are extremely useful for the synthesis of many important biochemical's and pharmaceuticals. Additionally, the use of stable isotopes has long been considered to be a promising tool in biomedical diagnosis. Furthermore, the past two decades have seen a tremendous leap forward in the development of very sophisticated instrumentation for the detection of disease and for probing biological structure and function. In conjunction with this a need for very complicated isotopically labeled materials has been on the increase.

Another area of application has become critical after the "9/11" tragedies. The use of stable isotopes in molecules (metabolites) for the rapid detection of threat agents (chemical and biological) is now in large demand. Current isotopic labeling precursors and techniques, however, have made this a very daunting task. Some advancements have been previously disclosed in U.S. Pat. No. 6,753,446, U.S. Pat. No. 6,709,645, U.S. Pat. No. 6,541,671, U.S. 2003158445, U.S. 2003153789, and U.S. 20030114.

In order to meet the urgent and growing demand, further high purity isotopically labeled compounds are needed.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to use known precursors such as [$^{13}$C]Methyl phenyl sulfide to produce labeled two carbon precursors such as [$^{13}$C$_2$]Ethyl phenyl sulfide. The labeled two carbon precursors can then be used to produce further previously unknown labeled compounds. High purity precursors ensure that the new compounds are also highly pure. For example, [$^{13}$C]Methyl phenyl sulfide in concentrations over 98 percent can be obtained using currently known techniques. As such, the previously unknown compounds herein disclosed are nearly 100 percent pure and are certainly over 90 percent pure.

BRIEF DESCRIPTION OF THE DRAWINGS

The accompanying figures, in which like reference numerals refer to identical or functionally similar elements throughout the separate views and which are incorporated in and form a part of the specification, further illustrate aspects of the embodiments and, together with the background, brief summary, and detailed description serve to explain the principles of the embodiments.

FIG. 7 illustrates a general formula for certain labeled compounds in accordance with aspects of the embodiments;

FIG. 8 illustrates another general formula for additional labeled compounds in accordance with aspects of the embodiments; and FIG. 9 illustrates yet another general formula for yet additional labeled compounds in accordance with aspects of the embodiments.

DETAILED DESCRIPTION

The following description contains a series of examples wherein previously known labeled compounds are processed to yield highly pure labeled compounds that are not previously known.

Synthesis of [1,2-$^{13}$C$_2$]ethyl phenyl sulfide

Figure 1:
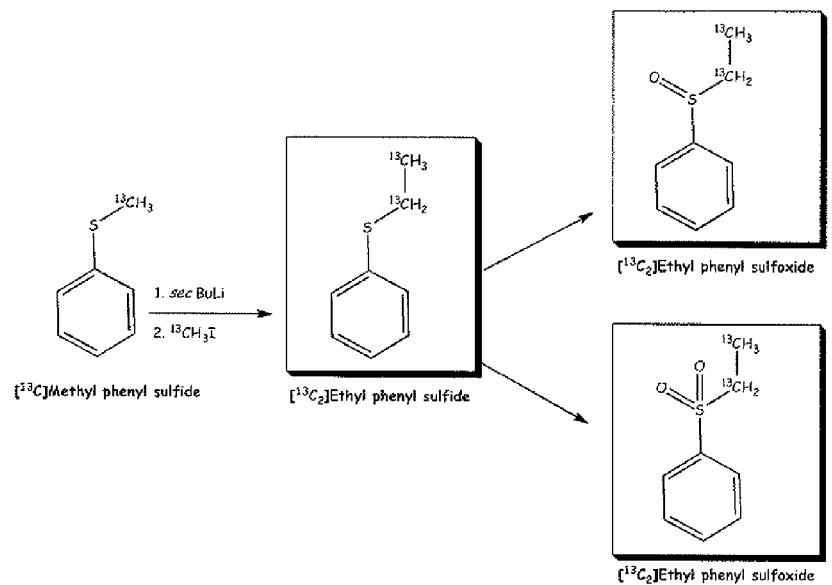
FIG. 1 illustrates synthesis and reactions of [1,2-13C2] ethyl phenyl sulfide in accordance with aspects of the embodiments.

FIG. 1 illustrates synthesis and reactions of [1,2-13C2] ethyl phenyl sulfide in accordance with aspects of the embodiments. A sample of [$^{13}$C]methyl phenyl sulfide (15.0 g, 0.119 moles, 1 equivalent) was dissolved in tetrahydrofuran (150 mL) in a 1 L round bottom flask. The reaction vessel was then cooled to −78° C. using a dry-ice/ethanol bath. To this cooled reaction sec-butyl lithium (1.4M/THF, 94.24 mL, 0.1319 moles, 1.3 equivalents) was added slowly over a 45-minute period. The reaction was allowed to stir for 30 minutes and then [$^{13}$C]methyl iodide (17.14 g, 0.1199 moles, 1 equivalent) was added slowly over a 40-minute period to the reaction. The reaction was allowed to stir for an additional hour and allowed to come to ambient temperature. After this period, water (100 mL) was added to the reaction. The reaction was then evaporated to remove tetrahydrofuran. To this mixture dichloromethane (150 mL) was added and the layers were separated. The organic layer was washed with water (2×20 mL) and then dried with sodium sulfate and then concentrated in vacuo to give the pure product (16.1 g, 91%). The product was suitable for use in subsequent reactions without purification.

2-(Phenylthio)[U-$^{13}$C$_2$]ethanol

Figure 2:
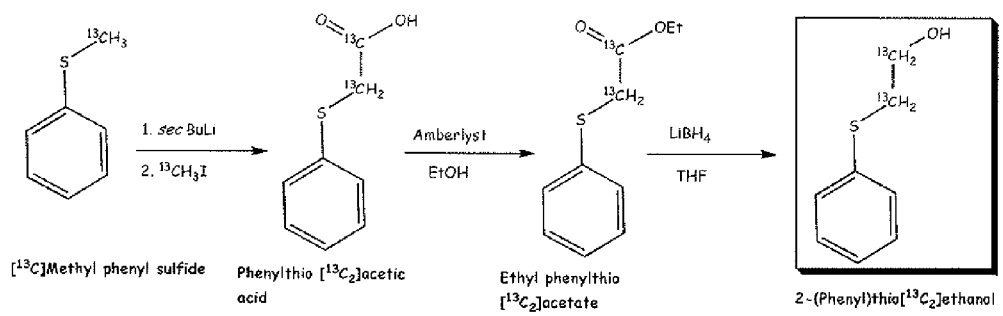
FIG. 2 illustrates synthesis of 2-phenylthio[1,2-13C2] ethanol in accordance with aspects of the embodiments.

FIG. 2 illustrates synthesis of 2-phenylthio[1,2-13C2] ethanol in accordance with aspects of the embodiments. Ethyl (phenylthio) [U-$^{13}$C$_2$]acetate (5.0 g, 25.22 mmol, 1.0 eq.) was dissolved in THF (50 mL) in a 250 mL round bottom flask, equipped with a magnetic stirrer, flushed with argon, and was cooled using and ice-water bath. Lithium borohydride (2.0M, 25.2 mL, 2.0 equivalents) was added dropwise over a period of seven minutes. The reaction mixture was permitted to warm to room temperature slowly as the ice melted, while stirring under argon. The reaction progress was monitored by TLC (at 1, 2, 8 and 24 hours) and $^{13}$C NMR (2, 8 and 24 hours) by taking an aliquot from the reaction mixture, dissolving in CDCl$_3$, and monitoring the disappearance of ethyl (phenylthio) [U-$^{13}$C$_2$]acetate and the subsequent appearance of the desired 2-(phenylthio)[U-$^{13}$C$_2$]ethanol. The reaction was complete after 24 hours. The reaction mixture was cooled using an ice-water bath then neutralized using 1 N HCl. The expected product was isolated by extraction with dichloromethane (3×50 mL). The organic layer was evaporated by vacuum distillation using a rotary evaporator to yield a pale yellow liquid (3.81 g, 97%), which was used without further purification.

Figure 3:
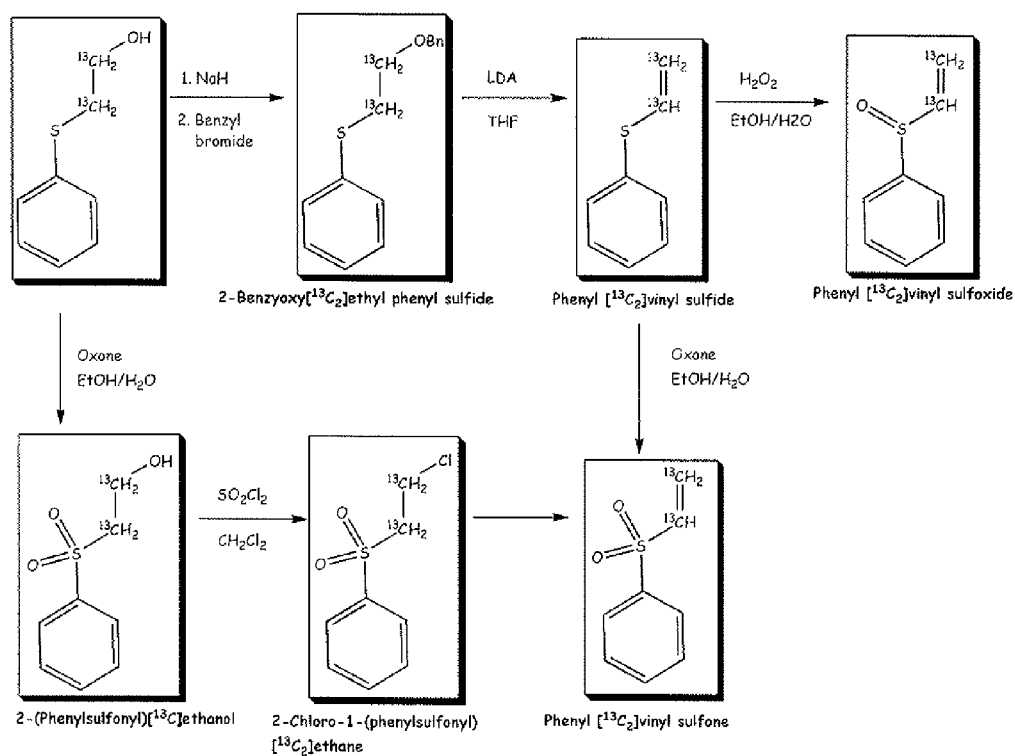
FIG. 3 illustrates reactions of 2-phenylthio[1,2-13C2]ethanol in accordance with aspects of the embodiments.

FIG. 3 illustrates reactions of 2-phenylthio[1,2-13C2]ethanol in accordance with aspects of the embodiments. 2-phenylthio[1,2-13C2]ethanol can be used as a precursor in the production of a number of isotopically tagged compounds.

2-Chloro[U-$^{13}$C$_2$]ethyl phenyl sulfone 2-(Phenylthio) [U-$^{13}$C$_2$]ethanol (1.0 g, 6.4 mmol, 1.0 equivalent) was dissolved in dichloromethane (10 mL) in a 50 mL round bottom flask, equipped with a magnetic stirrer. 1.09 grams of silica was placed into 1.0 mL of distilled water and then added to the stirred solution. The mixture was cooled using an ice-water bath. Once cooled, sulfuryl chloride (1.6 mL, 3.0 equivalents) was added dropwise over a period of approximately 3 minutes. The reaction mixture was permitted to warm to room temperature slowly as the ice melted. The reaction progress was monitored by $^{13}$C NMR (15 min.) by taking an aliquot from the reaction mixture, dissolving in CDCl$_3$, and monitoring the disappearance of 2-(phenylthio) [U-$^{13}$C]ethanol and the subsequent appearance of the desired 2-chloro[U-$^{13}$C]ethyl phenyl sulfone and was found to have gone to completion. The reaction mixture was cooled using an ice-water bath then neutralized using a saturated solution of sodium bicarbonate until it reached a pH of 8-9. The mixture was then extracted using dichloromethane (3×50 mL). The volatiles were removed by vacuum using a rotary evaporator to yield a white solid (1.1 g, 97%), which was used without further purification.

Phenyl[U-$^{13}$C$_2$]vinyl sulfone

2-Chloro[U-$^{13}$C$_2$]ethyl phenyl sulfone (1.1 g, 5.57 mmol, 1.0 eq.) was dissolved in THF (12.5 mL) in a 50 mL round bottom flask, equipped with a magnetic stirrer. The mixture was warmed to approximately 30° C. using a water bath. Once the solution warmed, triethylamine (1.2 mL, 1.5 eq.) dissolved in THF (10 mL) was added dropwise over a period of a minute. Salt formation was observed instantly. The reaction mixture was permitted to cool to room temperature. The reaction progress was monitored by $^{13}$C NMR (17 hrs.) by taking an aliquot from the reaction mixture, dissolving in CDCl$_3$, and monitoring the disappearance of 2-chloro[U-$^{13}$C$_2$]ethyl phenyl sulfone and the subsequent appearance of the desired phenyl[U-$^{13}$C$_2$]vinyl sulfone and was found to have gone to completion. The reaction mixture was filtered to remove the salt and washed with additional THF. The solid that formed was purified using column chromatography to yield a white solid (0.85 g, 88%).

Figure 4:
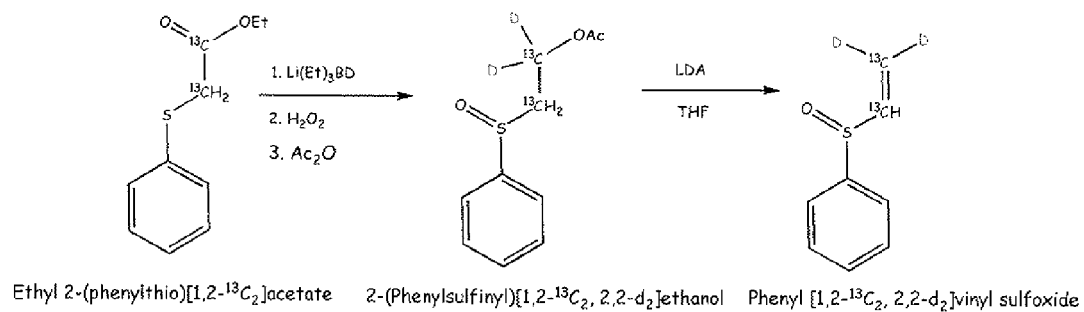
FIG. 4 illustrates synthesis of vinyl sulfoxides in accordance with aspects of the embodiments.

FIG. 4 illustrates synthesis of vinyl sulfoxides in accordance with aspects of the embodiments. Ethyl 2-(phenylthio) [1,2-$^{13}$C$_2$]acetate can be used to produce 2-(phenylsulfinyl) [1,2-$^{13}$C$_2$, 2,2-d$_2$]ethanol which can then in turn be used to produce phenyl[1,2-$^{13}$C$_2$,2,2-d$_2$]vinyl sulfoxide. The synthetic route can be used to produce all of the isotopic combinations of the vinyl sulfides, sulfoxides and sulfoxides.

Figure 5:
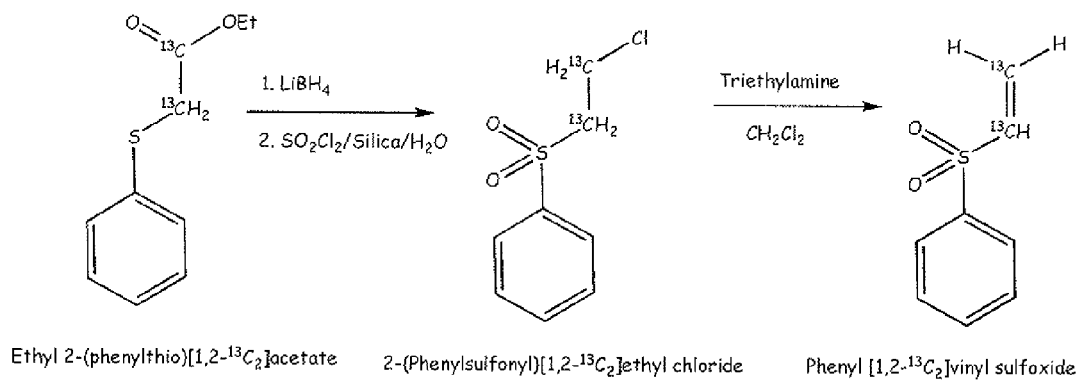
FIG. 5 illustrates an alternative preparation of vinyl sulfones in accordance with aspects of the embodiments.

FIG. 5 illustrates an alternative preparation of vinyl sulfones in accordance with aspects of the embodiments. Ethyl 2-(phenylthio)[1,2-$^{13}$C$_2$]acetate can be used to produce 2-(phenylsulfinyl)[1,2-$^{13}$C$_2$,2,2-d$_2$]chloride which can then in turn be used to produce phenyl[1,2-$^{13}$C$_2$,2,2-d$_2$]vinyl sulfoxide.

Figure 6:
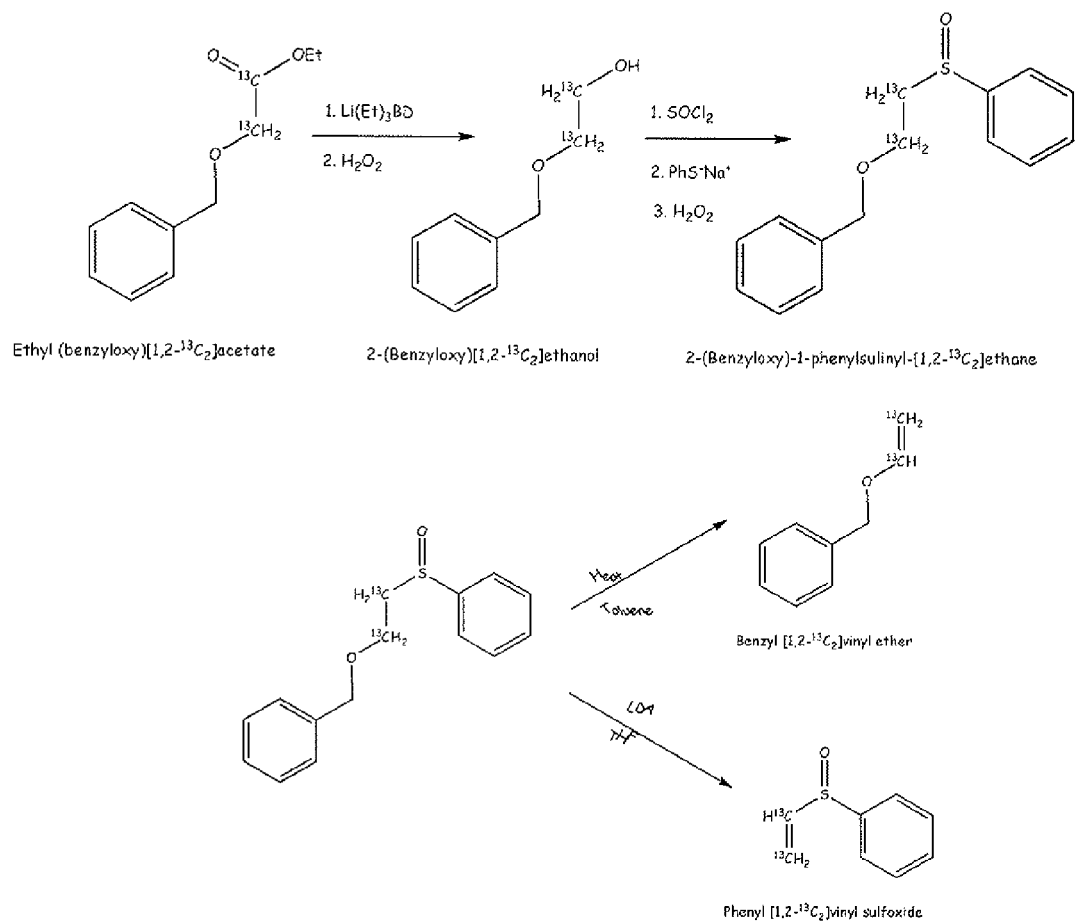
FIG. 6 illustrates the synthesis of isotopically labeled ethers and an alternative synthesis of vinyl sulfoxides and in particular the synthesis of benzyl[1,2-13C2]vinyl ether and phenyl[1,2-13C2]vinyl sulfoxide in accordance with aspects of the embodiments.

FIG. 6 illustrates the synthesis of isotopically labeled ethers and an alternative synthesis of vinyl sulfoxides and in particular the synthesis of benzyl[1,2-13C2]vinyl ether and phenyl[1,2-13C2]vinyl sulfoxide in accordance with aspects of the embodiments. A series of reactions beginning with ethyl (benzyloxy) [1,2-$^{13}$C$_2$]acetate produce a number of isotopically tagged intermediary compounds and culminate in the production of benzyl[1,2-$^{13}$C$_2$]vinyl ether and phenyl[1,2-$^{13}$C$_2$]vinyl sulfoxide.

FIGS. 7-9 illustrates general formulas for certain labeled compounds in accordance with aspects of the embodiments. The following examples illustrate techniques for the synthesis of compounds described by those general formulas.

2-(Phenylthio) [U-$^{13}$C$_2$]ethanol

Ethyl (phenylthio) [U-$^{13}$C$_2$]acetate (5.0 g, 25.22 mmol, 1.0 eq.) was dissolved in THF (50 mL) in a 250 mL round bottom flask, equipped with a magnetic stirrer, flushed with argon, and was cooled using and ice-water bath. Lithium borohydride (2.0M, 25.2 mL, 2.0 equivalents) was added dropwise over a period of seven minutes. The reaction mixture was permitted to warm to room temperature slowly as the ice melted, while stirring under argon. The reaction progress was monitored by TLC (at 1, 2, 8 and 24 hours) and $^{13}$C NMR (2, 8 and 24 hours) by taking an aliquot from the reaction mixture, dissolving in CDCl$_3$, and monitoring the disappearance of ethyl (phenylthio) [U-$^{13}$C$_2$]acetate and the subsequent appearance of the desired 2-(phenylthio)[U-$^{13}$C$_2$]ethanol. The reaction was complete after 24 hours. The reaction mixture was cooled using an ice-water bath then neutralized using 1 N HCl. The expected product was isolated by extraction with dichloromethane (3×50 mL). The organic layer was evaporated by vacuum distillation using a rotary evaporator to yield a pale yellow liquid (3.81 g, 97%), which was used without further purification.

2-Chloro[U-$^{13}$C$_2$]ethyl phenyl sulfone 2-(Phenylthio) [U-$^{13}$C$_2$]ethanol (1.0 g, 6.4 mmol, 1.0 equivalent) was dissolved in dichloromethane (10 mL) in a 50 mL round bottom flask, equipped with a magnetic stirrer. 1.09 grams of silica was placed into 1.0 mL of distilled water and then added to the stirred solution. The mixture was cooled using an ice-water bath. Once cooled, sulfuryl chloride (1.6 mL, 3.0 equivalents) was added dropwise over a period of approximately 3 minutes. The reaction mixture was permitted to warm to room temperature slowly as the ice melted. The reaction progress was monitored by $^{13}$C NMR (15 min.) by taking an aliquot from the reaction mixture, dissolving in CDCl$_3$, and monitoring the disappearance of 2-(phenylthio) [U-$^{13}$C]ethanol and the subsequent appearance of the desired 2-chloro[U-$^{13}$C]ethyl phenyl sulfone and was found to have gone to completion. The reaction mixture was cooled using an ice-water bath then neutralized using a saturated solution of sodium bicarbonate until it reached a pH of 8-9. The mixture was then extracted using dichloromethane (3×50 mL). The volatiles were removed by vacuum using a rotary evaporator to yield a white solid (1.1 g, 97%), which was used without further purification.

Phenyl[U-$^{13}$C$_2$]vinyl sulfone

2-Chloro[U-$^{13}$C$_2$]ethyl phenyl sulfone (1.1 g, 5.57 mmol, 1.0 eq.) was dissolved in THF (12.5 mL) in a 50 mL round bottom flask, equipped with a magnetic stirrer. The mixture was warmed to approximately 30° C. using a water bath. Once the solution warmed, triethylamine (1.2 mL, 1.5 eq.) dissolved in THF (10 mL) was added dropwise over a period of a minute. Salt formation was observed instantly. The reaction mixture was permitted to cool to room temperature. The reaction progress was monitored by $^{13}$C NMR (17 hrs.) by taking an aliquot from the reaction mixture, dissolving in CDCl$_3$, and monitoring the disappearance of 2-chloro[U-$^{13}$C$_2$]ethyl phenyl sulfone and the subsequent appearance of the desired phenyl[U-$^{13}$C$_2$]vinyl sulfone and was found to have gone to completion. The reaction mixture was filtered to remove the salt and washed with additional THF. The solid that formed was purified using column chromatography to yield a white solid (0.85 g, 88%).

What is claimed is:

1. A labeled compound having the structure:

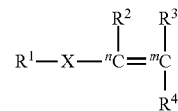

wherein n=12 or 13, and m=12 or 13 with the proviso that both n and m do not simultaneously equal 12; wherein X=S, SO, SO$_2$ or O; wherein R$^1$=Aryl; and wherein R$^2$, R$^3$, and R$^4$=H, $^2$H, $^3$H or Alkyl.

2. The labeled compound of claim 1 wherein n=13, m=13, X=SO, R$^1$=Phenyl; R$^2$=H, R$^3$=$^2$H, and R$^4$=$^2$H.

3. The labeled compound of claim 1 wherein n=13, m=13, X=SO, R$^1$=Aryl; R$^2$=H, R$^3$=$^2$H, and R$^4$=$^2$H.

4. The labeled compound of claim 1 wherein n=13, m=13, X=SO$_2$, R$^1$=Phenyl; R$^2$=H, R$^3$=H, and R$^4$=H.

5. The labeled compound of claim 1 wherein n=13, m=13, X=O, R$^1$=Phenyl; R$^2$=H, R$^3$=H, and R$^4$=H.

6. The labeled compound of claim 1 wherein n=13, m=13, X=SO, R$^1$=Phenyl; R$^2$=H, R$^3$=H, and R$^4$=H.

7. The labeled compound of claim 1 wherein n=13, m=13, X=S, R$^1$=Phenyl; R$^2$=H, R$^3$=$^2$H, and R$^4$=$^2$H.

* * * * *